(12) United States Patent
Liu

(10) Patent No.: US 10,481,119 B2
(45) Date of Patent: Nov. 19, 2019

(54) FORCE SENSOR ARRAY HAVING AN ENERGY-ABSORBING FILM LAYER WITH AN ELASTIC DEFORMABILITY THAT CONVERTS KINETIC ENERGY INTO HEAT ENERGY

(71) Applicant: Foshan Sensicfusion Technology Co., LTD, Foshan (CN)

(72) Inventor: Chang Liu, Foshan (CN)

(73) Assignee: Foshan Sensicfusion Technology Co., LTD, Foshan (CN)

( * ) Notice: Subject to any disclaimer, the term of this patent is extended or adjusted under 35 U.S.C. 154(b) by 121 days.

(21) Appl. No.: 15/831,309

(22) Filed: Dec. 4, 2017

(65) Prior Publication Data

US 2019/0170675 A1  Jun. 6, 2019

(51) Int. Cl.
*G01N 27/16* (2006.01)
*G01L 5/16* (2006.01)
*G01L 19/14* (2006.01)
*G01L 1/22* (2006.01)

(52) U.S. Cl.
CPC .............. *G01N 27/16* (2013.01); *G01L 1/225* (2013.01); *G01L 5/16* (2013.01); *G01L 19/148* (2013.01)

(58) Field of Classification Search
None
See application file for complete search history.

(56) References Cited

U.S. PATENT DOCUMENTS

2009/0294385 A1* 12/2009 Tajima ................. B01D 61/145
                                                             210/808

\* cited by examiner

*Primary Examiner* — Andre J Allen
(74) *Attorney, Agent, or Firm* — Aslan Law, P.C.

(57) ABSTRACT

A force sensor array that includes a circuit board, a plurality of gas pressure sensors arranged on the circuit board, and an energy-absorbing film layer covering a gas nozzle of each gas pressure sensor. The energy-absorbing film layer has an elastic deformability, and the energy-absorbing film layer can convert impact kinetic energy into heat energy.

8 Claims, 1 Drawing Sheet

FORCE SENSOR ARRAY HAVING AN ENERGY-ABSORBING FILM LAYER WITH AN ELASTIC DEFORMABILITY THAT CONVERTS KINETIC ENERGY INTO HEAT ENERGY

TECHNICAL FIELD

The present invention relates to the technical field of sensor, particularly to a force sensor array.

BACKGROUND OF THE INVENTION

With a wide range of applications, force sensor can be used for weighing, contact detection and appearance test. In robot applications, it can be used for contact detection. Such products can be achieved through a variety of principles, most of which are based on the deformation caused by stress or variation of stress.

Existing force sensors can achieve high sensitivity, but have poor resistance to overload and bursting. They are easily damaged under overload pressure or fast changing high impact pressure. The FSS force sensor series produced by the United States Honeywell applies to fine weighing in the medical field, but its price is high and it has no additional circuit. The overload capacity of the product is only 1.5 times the full scale, and its silicon film is easy to crack under high impact.

SUMMARY OF THE INVENTION

Considering the shortcomings of the prior art, the purpose of this invention is to provide a force sensor array with high sensitivity and high bursting resistance.

To achieve the said purpose, the utility model adopts the following technical solution.

A force sensor array, characterized in that it comprises: a circuit board, a plurality of gas pressure sensors arranged on the circuit board, and an energy-absorbing film layer covering the gas nozzle of each gas pressure sensor; the said energy-absorbing film layer has a certain elastic deformability, and can convert impact kinetic energy into heat energy.

As a further explanation of the said solution, the said gas pressure sensor is a planar pressure sensor, and an airflow hole corresponding to the gas nozzle of the gas pressure sensor is provided on the circuit board.

As a further explanation of the said solution, the said force sensor array includes a housing, a groove is provided on the housing, and the said circuit board is suspended at the bottom of the groove through a column.

As a further explanation of the said solution, the said gas nozzle is convexly disposed on the top of the gas pressure sensor, and each gas pressure sensor is encapsulated in a gum base.

As a further explanation of the said solution, the said energy-absorbing film layer adopts a nanoporous material energy-absorbing structure, comprising one or more layers of polymer material shell and nanoporous material mixture liquid encapsulated in the polymer material shell, and the said nanoporous material mixture liquid is a mixture of nanoporous material and non-infiltrative liquid.

As a further explanation of the said solution, when pressure is slowly applied, the energy-absorbing film layer shows the characteristics of solid to transfer pressure; different gas pressure sensors sense different pressure values during stress; the circuit board collects the pressure values fed back by the gas pressure sensors to show the spatial distribution of stress.

As a further explanation of the said solution, when impact bursting force is applied to the energy-absorbing film layer, the non-infiltrative liquid in the energy-absorbing film layer is in a flowing state, so as to absorb energy and convert kinetic energy into heat energy.

As a further explanation of the said solution, the gas pressure sensors are arrayed on the circuit board. The beneficial effect of this invention is as follows:

Through the provision of the energy-absorbing film layer, circuit board and other structures, when pressure is applied slowly, the energy-absorbing film layer of this invention shows the characteristics of solid to transfer pressure; different gas pressure sensors sense different pressure values during stress. The circuit board collects the pressure values fed back by the gas pressure sensors to show the spatial distribution of stress. When impact bursting force is applied to the energy-absorbing film layer, the energy-absorbing film layer converts kinetic energy into heat energy for dissipation, which can buffer impact and absorb more than 95% of the impact energy to improve the bursting resistance of the entire array. In addition, it is cost-effective.

DESCRIPTION OF THE DESIGNATIONS IN THE DRAWINGS

Figure 1:
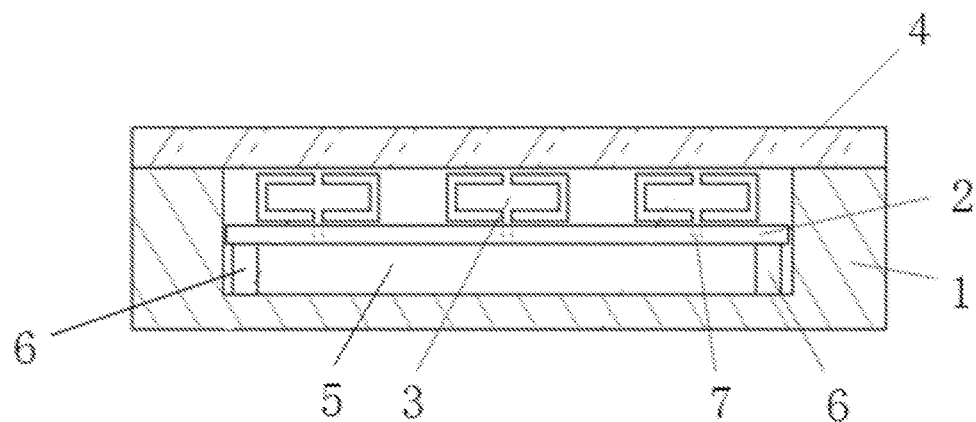
FIG. 1 is the schematic diagram of the force sensor array as described in Embodiment 1 of this invention.

1: Housing, 2: Circuit board, 3: Gas pressure sensor, 4: Energy-absorbing film layer, 5: Groove, 6: Column, 7: Airflow hole, 8: Gum base

DETAILED DESCRIPTION OF THE PREFERRED EMBODIMENTS

In the description of this invention, it should be noted that the terms indicating orientation and positional relationship (such as "center", "transverse", "longitudinal", "length", "width", "thickness", "upper", "lower", "front", "back", "left", "right", "vertical", "horizontal", "top", "bottom", "inner", "outer", "clockwise" and "counterclockwise") are based on the orientation and positional relationship shown in the drawings. Such terms are only used for facilitating the description of this invention and simplifying the description rather than indicating or implying that the indicated devices or components must have a particular orientation or be structured and operated in a particular orientation, and shall not be construed to limit the specific scope of protection of this invention.

In this invention, unless expressly provided and limited otherwise, the terms "assembled", "connected" and "connection" shall be broadly understood, such as "fixed connection", "detachable connection", "integrally connected", "direct connection", "connection through an intermediate medium" and "two components whose interiors are connected". Those of ordinary skill in the art may understand the specific meanings of the above terms in this invention according to specific situations.

In this invention, unless expressly provided and limited otherwise, the first feature above or beneath the second feature may include direct contact between the first feature and the second feature, or indirect contact between the first feature and the second feature through other features between them. Moreover, the first feature "above", "below" and "over" the second feature includes that the first feature is immediately or obliquely above the second feature or merely indicates that the first feature is at a higher level than the second feature. The first feature "above", "below" and "under" the second feature includes that the first feature is immediately or obliquely below the second feature or merely indicates that the first feature is at a lower level than the second feature.

This invention will be further described by referring to the accompanying drawings that illustrate the specific embodiments of this invention, from which its technical solution and beneficial effect will be more evident. The embodiments described below by referring to the accompanying drawings are illustrative and intended to explain this invention and shall not to be construed to limit this invention.

Embodiment I

As shown in FIG. 1, a force sensor array, comprising: a housing 1, a circuit board 2, a plurality of gas pressure sensors 3 and an energy-absorbing film layer 4, a groove 5 is provided on the housing 1, the said circuit board 2 is suspended at the bottom of the groove 5 through the column 6, the said pressure sensors 3 are arrayed on the circuit board 2, and the said energy-absorbing film layer 4 covers the gas nozzle of each gas pressure sensor 3.

The said gas pressure sensor 3 is a planar pressure sensor, and an airflow hole 7 corresponding to the gas nozzle is provided on the circuit board 2 to improve the detection accuracy.

The said energy-absorbing film layer 4 is a flexible film, which has a certain elastic deformability, and can convert impact kinetic energy into heat energy for strong impact resistance. In this embodiment, the energy-absorbing film layer preferably adopts a nanoporous material energy-absorbing structure, comprising one or more layers of polymer material shell and nanoporous material mixture liquid encapsulated in the polymer material shell, and the said nanoporous material mixture liquid is a mixture of nanoporous material and non-infiltrative liquid.

When pressure is slowly applied, the energy-absorbing film layer shows the characteristics of solid to transfer pressure; different gas pressure sensors sense different pressure values during stress. The circuit board collects the pressure values fed back by the gas pressure sensors to show the spatial distribution of stress. When impact bursting force is applied to the energy-absorbing film layer, the non-infiltrative liquid in the energy-absorbing film layer is in a flowing state to absorb energy and convert kinetic energy into heat energy for dissipation, which can buffer impact and absorb more than 95% of the impact energy to improve the bursting resistance of the entire array.

Embodiment II

Figure 2:
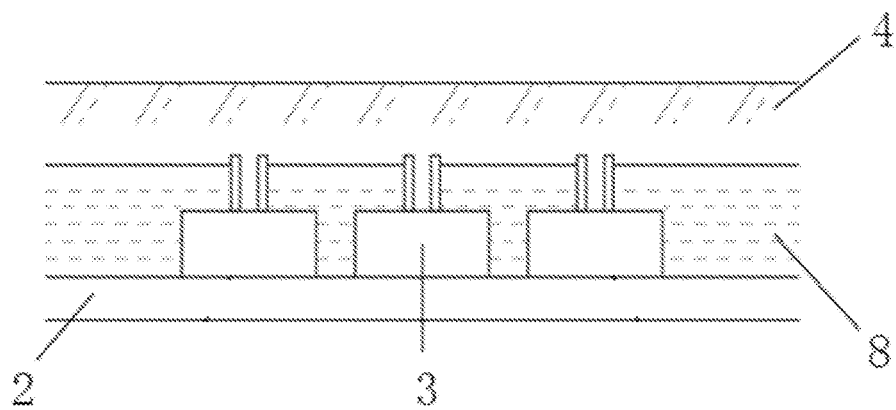
FIG. 2 is the schematic diagram of the force sensor array as described in Embodiment 2 of this invention.

As shown in FIG. 2, a force sensor array provided in this embodiment has basically the same structure as the first embodiment except that the housing is removed, and a convex gas nozzle is provided on the gas pressure sensor 3, and each gas pressure sensor 3 is encapsulated in a gum base 8.

Through the above description of the structure and principle, it should be understood by those skilled in the art that this invention is not limited to the above specific embodiments, and the improvements and replacements adopting the publicly known techniques in the art based on this invention fall within the scope of protection of this invention, and the scope of protection of this invention shall be defined by the claims and their equivalents.

The invention claimed is:

1. A force sensor array comprises:
   a circuit board,
   a plurality of gas pressure sensors arranged on the circuit board, and
   an energy-absorbing film layer covering a gas nozzle of each gas pressure sensor; wherein
   said energy-absorbing film layer has an elastic deformability, and
   said energy-absorbing film layer can convert impact kinetic energy into heat energy.

2. The force sensor array according to claim 1, wherein the said gas pressure sensor is a planar pressure sensor, and an airflow hole corresponding to the gas nozzle of the gas pressure sensor is provided on the circuit board.

3. The force sensor array according to claim 2, further comprising:
   a housing, and
   a groove is provided on the housing, wherein
   the said circuit board is suspended at the bottom of the groove through a column.

4. The force sensor array according to claim 1, wherein the said gas nozzle is convexly disposed on the top of the gas pressure sensor, and each gas pressure sensor is encapsulated in a gum base.

5. The force sensor array according to claim 1, wherein the said energy-absorbing film layer adopts a nanoporous material energy-absorbing structure, comprising one or more layers of polymer material shell and nanoporous material mixture liquid encapsulated in the polymer material shell, and the said nanoporous material mixture liquid is a mixture of nanoporous material and non-infiltrative liquid.

6. The force sensor array according to claim 5, wherein when pressure is slowly applied, the energy-absorbing film layer shows the characteristics of solid to transfer pressure; different gas pressure sensors sense different pressure values during stress; the circuit board collects the pressure values fed back by the gas pressure sensors to show the spatial distribution of stress.

7. The force sensor array according to claim 5, wherein when impact bursting force is applied to the energy-absorbing film layer, the non-infiltrative liquid in the energy-absorbing film layer is in a flowing state, so as to absorb energy and convert kinetic energy into heat energy.

8. The force sensor array according to claim 1, wherein the gas pressure sensors are arrayed on the circuit board.

* * * * *